(12) United States Patent
Michelson

(10) Patent No.: US 6,609,322 B1
(45) Date of Patent: Aug. 26, 2003

(54) GUN HANDLE DESIGN

(76) Inventor: Gary Karlin Michelson, 438 Sherman Canal, Venice, CA (US) 90291

( * ) Notice: Subject to any disclaimer, the term of this patent is extended or adjusted under 35 U.S.C. 154(b) by 0 days.

(21) Appl. No.: 09/618,197

(22) Filed: Jul. 18, 2000

Related U.S. Application Data

(63) Continuation of application No. 08/112,426, filed on Aug. 26, 1993, now Pat. No. 6,129,740, which is a continuation of application No. 07/692,583, filed on May 13, 1991, now abandoned, which is a continuation of application No. 07/341,848, filed on Apr. 24, 1989, now abandoned.

(51) Int. Cl.⁷ ............................................. F41C 23/10
(52) U.S. Cl. ........................................ 42/71.02; 42/7
(58) Field of Search ..................... 42/7, 49.01, 49.02, 42/50, 71.02

(56) References Cited

U.S. PATENT DOCUMENTS

| | | | |
|---|---|---|---|
| 156,431 A | * 11/1874 | Luce | 42/7 |
| 547,447 A | * 10/1895 | Paquot et al. | 42/7 |
| 1,028,032 A | * 5/1912 | Krag | 42/7 |
| 1,202,707 A | * 10/1916 | Grieco | 42/7 |
| 1,349,345 A | * 8/1920 | Payne | 42/50 |
| D167,034 S | 6/1952 | Gottlieb et al. | |
| 2,874,502 A | * 2/1959 | Lockwood | 42/71.02 |
| 3,019,673 A | 2/1962 | Sjostkand et al. | |
| 3,128,571 A | * 4/1964 | Herrett | 42/71.02 |
| 3,167,876 A | * 2/1965 | Milroy, Jr. | 42/7 |
| D230,974 S | * 3/1974 | Howlett | D22/1 |
| 4,330,093 A | 5/1982 | Chapman, Jr. | 242/7.17 |
| D272,278 S | 1/1984 | Green et al. | D24/26 |
| D277,029 S | 1/1985 | Blake, III et al. | D24/26 |
| 4,669,769 A | 6/1987 | Polder, Jr. | 294/19.1 |
| 4,733,671 A | 3/1988 | Mehl | 128/310 |
| 4,777,948 A | 10/1988 | Wright | 128/312 |
| 5,592,769 A | * 1/1997 | Villani | 42/50 |
| 5,768,817 A | * 6/1998 | Simons | 42/71.02 |

FOREIGN PATENT DOCUMENTS

| | | | | |
|---|---|---|---|---|
| CH | 73402 | * | 10/1916 | 42/71.02 |
| DE | 2618074 | * | 11/1977 | 42/7 |
| FR | 550415 | * | 3/1923 | 42/7 |
| FR | 2485179 | * | 12/1981 | 42/7 |

OTHER PUBLICATIONS

Mathews LTD, Olympic records held by VOSTOK, Sep. 1962, Shooting Times and Country Magazine, one page.*
Colt Case, Guns and Ammo, Mar. 1976, Colt Case, pp. 74–75.*
English translation of Swiss Patent No. 73402 (J. Bocksberger and sons, Dec. 17, 1914).
Electrical Construction & Maintenance, p. 151, Jan. 1978.
Industrial Design, p. 56, Sep. 1968.
Ramset catalog, Winchester Group, Olin Corp., Form B–552, 1969.
Remington Powder Actuated Fastening Systems, p. 5, Oct. 1974.

* cited by examiner

Primary Examiner—Stephen M. Johnson
(74) Attorney, Agent, or Firm—Martin & Ferraro, LLP

(57) ABSTRACT

An ergonomic and proprioceptive handle design for instruments is disclosed. The handle can be used with a wide variety of medical instruments, such as a rongeur, as well as other instruments, such as guns and staplers.

12 Claims, 6 Drawing Sheets

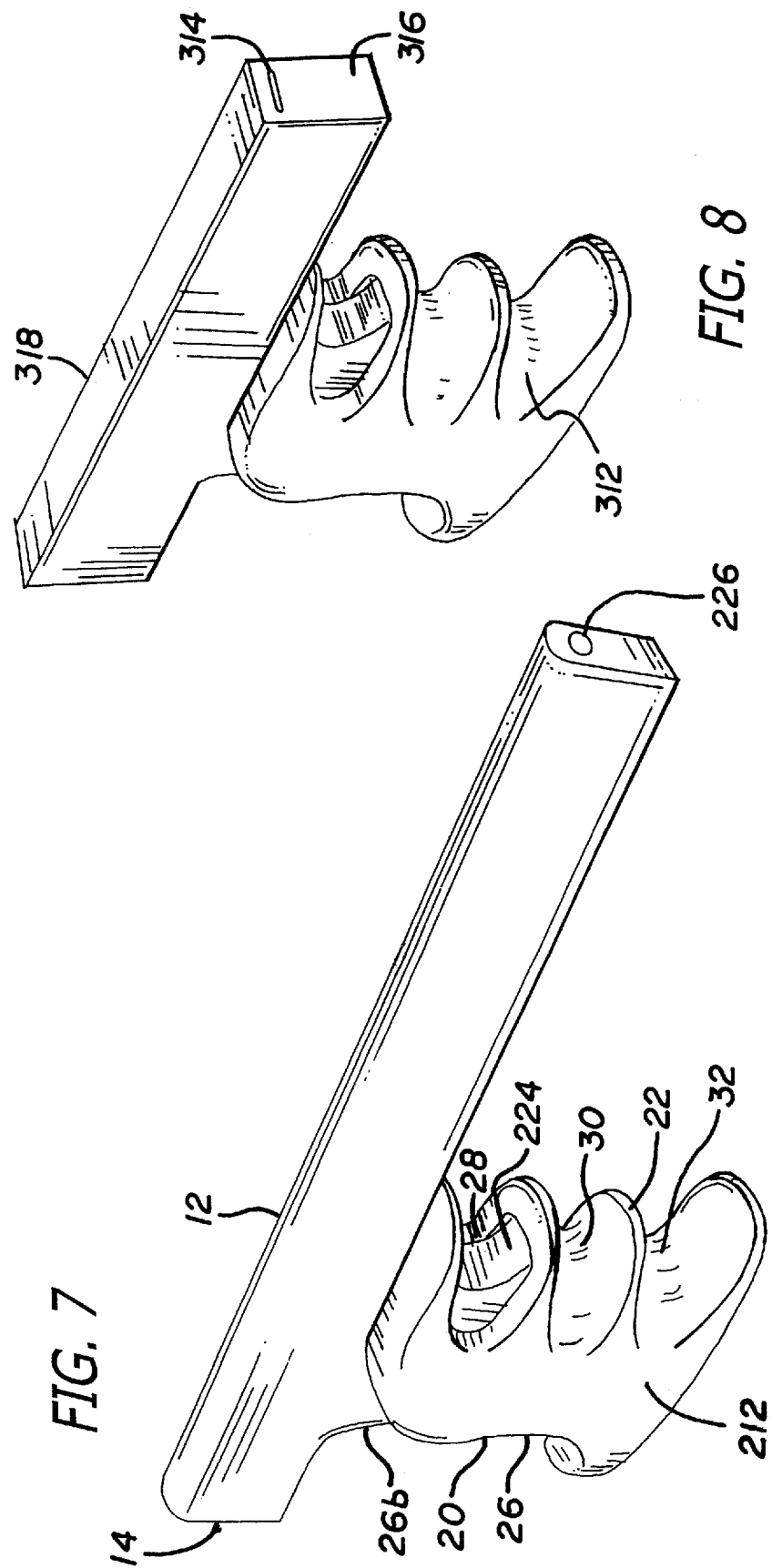

GUN HANDLE DESIGN

This is a continuation of application Ser. No. 08/112,426, filed Aug. 26, 1993, now U.S. Pat. No. 6,129,740, which is a continuation of application Ser. No. 07/692,583, filed May 13, 1991, abandoned, which is a continuation of application Ser. No. 07/341,848, filed Apr. 24, 1989, abandoned, all of which are incorporated herein by reference.

BACKGROUND

Hand powered instruments useful for biting tissues, known as rongeurs are common in the field of surgery. While there are many variations designed for use by one hand, the most common by far, would be the Pituitary, Kerrison, and Leksell types.

Prior hand operated rongeurs of the pituitary type have been characterized by a scissors like construction, with thumb and index finger grip holes, or of the Kerrison type using the thenar-palm line and four fingered handle. In these and other available designs, the forefinger is used to actuate the instrument from a position offset from the actuating operating mechanism so that the force required to close and open the instrument also translates in part into an upward displacement of the operating shaft and tip of the instrument. Not infrequently the surgeon finds it necessary to post the tip of the instrument into healthy tissue in order to limit the movement of the tip before biting or cutting the tissue to be removed. This injures healthy tissue. Also, due to the orientation of the hand and fingers, the location of the tip of the instrument is difficult to be mentally perceived, much less controlled, by the surgeon.

There is, therefore, a need for an improved handle for surgical instruments.

SUMMARY OF THE PRESENT INVENTION

The present invention consists of a rongeur having a main body portion which is the longitudinal proximal extension of the working shaft of the instrument. The most rearward portion of the body portion extends for approximately one inch over the dorsum of the hand, specifically in the notch formed by the junction of the thumb and index finger to the hand. Just distal to the proximate end of the body member, is the rear arcuate handle, the arc facing the rear end of the instrument. This rear handle is affixed to the body portion at essentially 90 degrees to the long axis of the body portion and will anatomically conform to the shape of the thenar eminence (the prominence of the muscles of the thumb) when the hand is in the "Bang Bang", "Fake Gun" or index finger pointing with the thumb extended position. In fact, the hand in grasping the instrument will, by means of said fixed proximal handle contour, be coaxed into assuming the desired position.

The lower portion of the rear handle continues, where it may either become convex or continue in line with the thenar portion, in which event said member would follow the shape of the thenar proximal, but would be more ulnar (towards the little finger side of the hand) such that in either case the ulnar border of the hand would be driven more proximal beneath the thenar's and with a tendency for the wrist, if unresisted, to assume a more extended (cocked-up) position. Spaced from the rear handle member of the instrument is a front downwardly disposed, pivotable arcuate handle member, of a length sufficient to accommodate the long, ring and little fingers of the hand. The lower portion of the front handle may be curved to facilitate finger placement and provide for a cradling of the lowest finger, thereby providing for a better feel and more control. A spring mechanism associated with the front handle, is utilized to urge the front handle to its original forward position. In alternative embodiments, the front handle may be fixed and provided with a trigger housing and mechanism for activating the rongeur. For example, if the rongeur is electrically powered, the trigger within the housing would activate the rongeur.

The instrument of the present invention is grasped quite differently from all other prior surgical instruments in that the index finger is separated from the remaining three fingers and is left extended along the main shaft of the instrument, pointing, while the three remaining fingers are wrapped around the unusually short front handle or trigger. The thumb is fully extended and may come to rest in more distal position, relative to its natural resting position and to the other fingers of the hand, as the shape of the rear handle urges the thumb portion of the hand forward and the wrist into a more extended (cocked-up) position. The part of the body portion coming to lie between the thumb and index fingers, which are relatively opposed, is called the "pinch pad" area of the body portion of the instrument.

The following advantages of the present invention are a product of the handle design and the induced finger, hand, and wrist positions:

1. Ambidextrous.
2. Anatomic to the working position profile of the inside of the partially closed hand.
3. Anatomic to and thus induces the optimal functional finger, hand and wrist positions.
4. Recruits the "Automatic Hand Effect" to optimize the instrument function. If no attempt is made to inhibit it, it can be observed that taking the fingers from the fully extended position with the hand straight out to the semi-closed finger grasping position, causes the wrist to go into the "cocked-up" position automatically. This effect is deliberately elicited by the handle design and is beneficial in at least two ways. Firstly, it allows for the proper alignment, discussed below, and secondly it improves the finger flexion function, as described below in Item 6.
5. While the handle design deliberately elicits the described wrist extension, this in fact results in the absolute longitudinal alignment of the surgical instrument through the hand and wrist with the forearm.
6. Finger flexion. The means of operating these instruments is facilitated by wrist extension. This is easily proven by assuming the opposite position and attempting to make a fist with the wrist fully flexed.
7. Elimination of the operating shaft/hand vertical displacement, increasing control.
8. Maximalization of hand contact is achieved for added control. The thumb and index fingers contact the body portion throughout their entire length. The palm engages the handle across its entire breadth, with the thenar engaging and almost encircling the rear handle portion. The three remaining fingers literally wrap around the front handle portion.
9. Minimalization of skin contact pressures.
10. Fits all size hands, because the lower three fingers wrap the pivotal front handle or trigger, and since it does not matter whether it is more proximally or distally, the handle will function well, and feel good to hands of all sizes.
11. Increased mechanism capacitance of springs and the like in the body portion.
12. The surgeon's hand is not exposed to any sharp or moving parts.

13. Enhanced instrument stability. The opposition of the thumb and index fingers on either side of the "pinch pad" stabilizes the instrument against side to side movement, while the instrument is also stabilized against any up and down movement by both the rear and front handles, which have both upper and lower contoured stops.

14. Ergonomic. The handle is biomechanically engineered to facilitate the human hand function in its operation.

15. Proprioceptive. Proprioception or kinesthetic sense is the ability to correctly spacially locate a bodily part without the use of vision. This allows one to easily place a finger in the ear or on the tip of the nose, even with the eyes closed. The index finger first, and the tactile pulp of the thumb secondly, are the most richly invested with this kinesthetic capacity. Prior rongeurs have failed to take advantage of this, and have allowed both the index finger and thumb to face away from the intended target, or to be curled up in and upon themselves. The present design aligns the index finger and thumb along the longitudinal axis of the instrument such that they always point exactly at the target, and thereby facilitate the accurate placement of the instrument by the operator, without the need to visually monitor that action. This is extremely important as it allows the surgeon to remain focused at the surgical site even as the instrument is passed into and away from that site, and without the need for the surgeon to perform continuing and repetitive disruptive reorientations.

16. The absence of reactive tip excursion. Since the typical rongeur provides for only two points of hand fixation to the handle, when an attempt is made to operate the instrument by imparting of force at the handle, there is an excursion of the tip, according to Newton's 3rd law of action and equal reaction, such that the tip is moved from the intended targeted tissue. With the present invention, stabilization of the instrument distal to the application of the trigger force, at the "pinch pad", allows for the requisite reactionary counter force required to neutralize the proximal force, thereby leaving the tip free of any undesirable excursion during the instrument's operation.

17. The design is compact and requires reduced operating space because of the absence of any vertical displacement of the grasped area from the instrument shaft axis and by aligning the instrument axis and containing the entire handle within the hand. As a direct result, smaller incisions and less wound retraction is required for the operation of instruments with handles so designed.

18. Ultra-low profile.

19. Enhanced sight visualization as the view of the tip is unobstructed by any protrusions.

20. Line of sight targeting. The instrument design facilitates the accurate aiming of the instrument, much like sighting a rifle. The extended index finger and aligned instrument shaft are like the rifle barrel, while the instrument tip is the front bead, and the anatomical "V" of the thumb and index finger, bisected by the proximate handle extension, is the rear targeting site.

21. Universality. This handle's design can be utilized for a large variety of previously disparate rongeur types, thereby facilitating surgery, in that each instrument feels and operates in the identical fashion.

22. Increased comfort.

23. Increased maneuverability.

24. A stronger and more rigid instrument. The overall length of the instrument and displacement of the handle from the axis of the instrument are minimized by aligning the instrument within the hand and containing the handle therein. Reduction of the instrument length and the displacement of the points of application of force to the extended lever arm results in a more rigid and stronger construct.

25. More durable.

OBJECTS OF THE PRESENT INVENTION

It is therefore an object of the present invention to provide an improved handle for a medical instrument that is ergonomic;

It is another object of the present invention to provide an improved handle for a medical instrument that is easier to use;

It is another object of the present invention to provide an improved handle for a medical instrument that automatically correctly positions the hand of the user on the instrument;

It is another object of the present invention to provide an improved handle for a medical instrument that is more comfortable and causes less fatigue during use;

It is another object of the present invention to provide an improved handle for a medical instrument that is more durable;

It is another object of the present invention to provide an improved handle for a medical instrument provides for improved proprioception of the instrument tip;

It is still another object of the present invention to provide an improved handle for a medical instrument that is more stable.

These and other objects of the present invention will be apparent from a review of the following specification and the accompanying drawings.

BRIEF DESCRIPTION OF THE DRAWINGS

FIG. 5 also illustrates that the instrument is ambidextrous.

FIGS. 6–8 are perspective views an alternative embodiment of the invention.

DETAILED DESCRIPTION OF THE DRAWINGS

Figure 1:
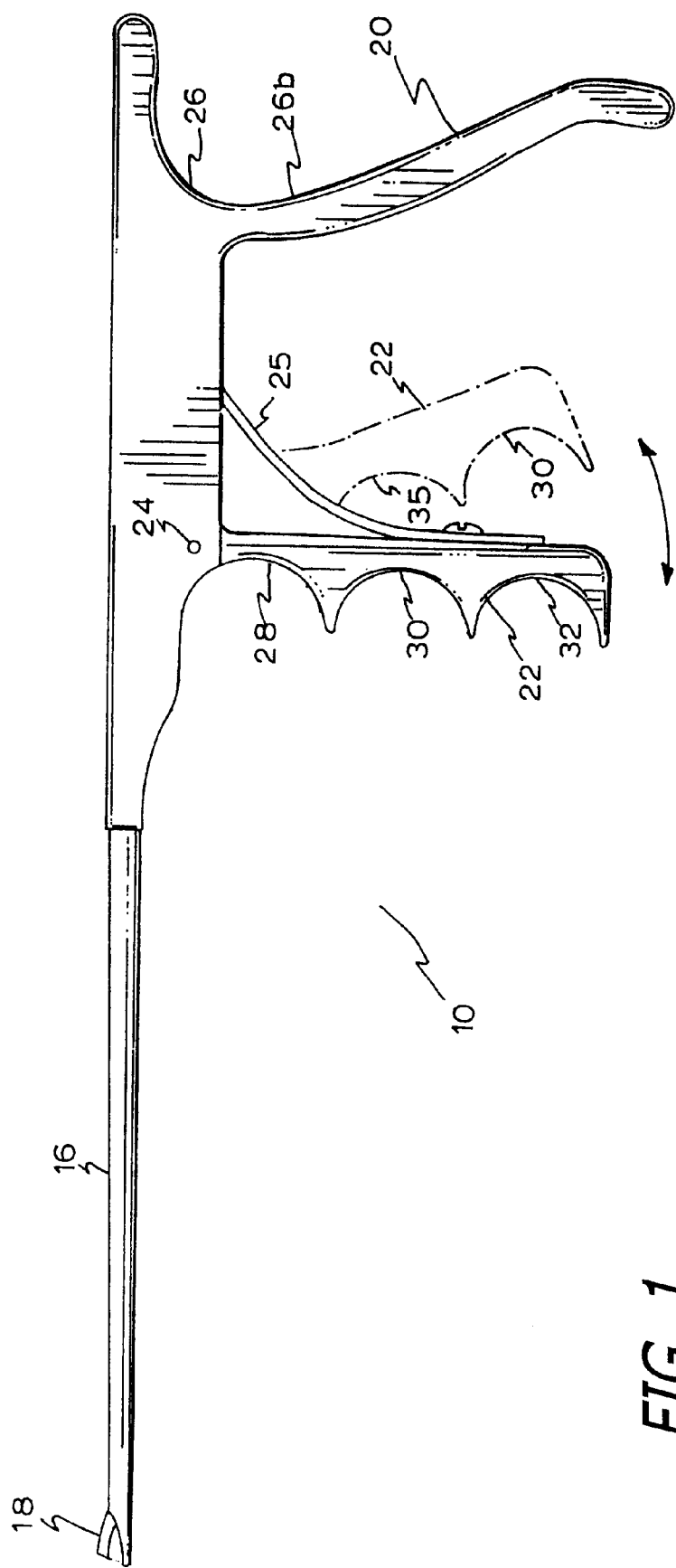
FIG. 1 is a side elevational view of a surgical instrument constructed in accordance with the present invention.

Referring to FIGS. 1–5, there is shown a first embodiment of a surgical instrument 10 constructed in accordance with the present invention. The instrument 10 is a hand operated rongeur having a body portion 12 with a depending rear handle 20 and front handle 22. The cross section of the body portion 12 is generally rectangular. A working shaft 16 extends distally from the body which terminates in a rongeur biting mechanism 18 of conventional construction. The rear handle 20 is fixed. The forward handle 22 is connected to operating mechanisms contained within the body portion 12 and is pivoted about a pivot pin 24 or other means for movement to actuate the biting mechanism in response to a squeezing movement of the surgeon's hand.

The body portion 12 has a proximal extension 14 at its rear end which joins the rear handle 20 to form a rearwardly facing continuous curved portion 26. The proximal extension 14 extends for approximately one inch over the dorsum of the hand, specifically in the notch formed by the junction of the thumb and index finger.

The body portion 12 in line with the longitudinal axis of the working shaft 16 of the instrument 10, has a width which, in the preferred embodiment, is approximately 8 mm. The body portion 12 has a length in the preferred embodiment of 9 cm. The shaft of the instrument is, approximately 15 cm. Thus the instrument 10 has an overall length of about 24 cm.

The rear handle 20 extends substantially at right angles to the body portion 12 and is in the shape of a rearwardly facing thenar fitting curve 26b formed to lie comfortably in the hand, cradled along the thenar-palm of the hand such that the palm closely fits up to the instrument with the thumb and forefinger naturally extending on both sides of the body portion 12, each projecting distally along a respective side at the top of the body portion 12. The rear handle 22 anatomically conforms to the shape of the thenar eminence (the prominence of the muscles of the thumb) when the hand is in the make-believe gun of childs play position with the index finger pointing and the thumb in an extended position. In fact, the hand, in grasping the instrument, will, by means of the fixed rear handle contour, be coaxed into assuming the described position.

The portion of the rear handle 20 below of the thenar cradle portion, continues where it may form a reverse curvature to become convex or continue in line with the thenar portion such that the ulnar border of the hand is driven to a more proximal position beneath the thenar's and with a tenancy for the wrist to assume a more extended or cocked-up position.

Figures 2, 4:
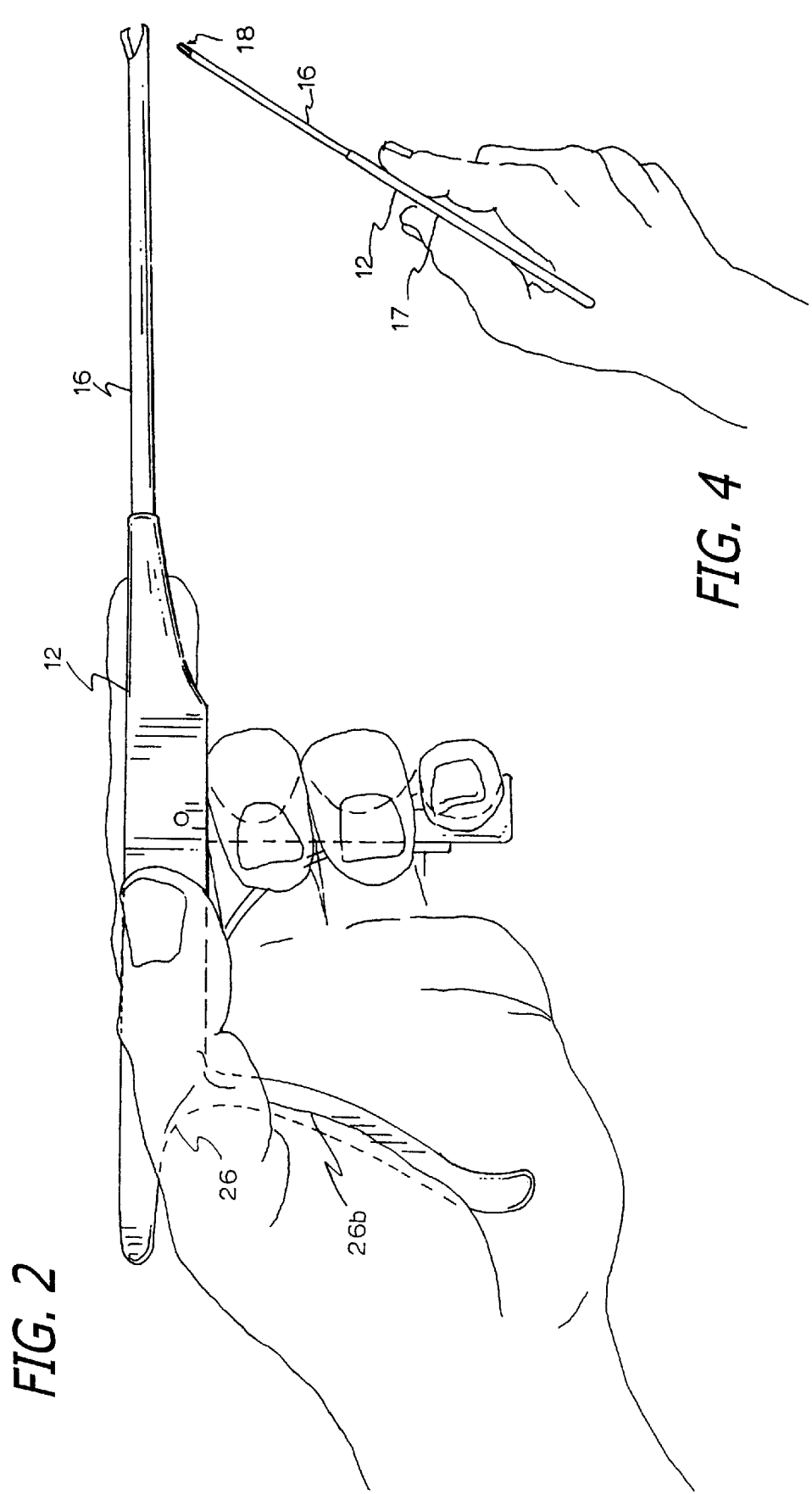
FIG. 2 is a side view of the instrument of FIG. 1 being held in the hand.
FIG. 4 is a top perspective view of the surgical instrument held in the hand.
Figure 3:
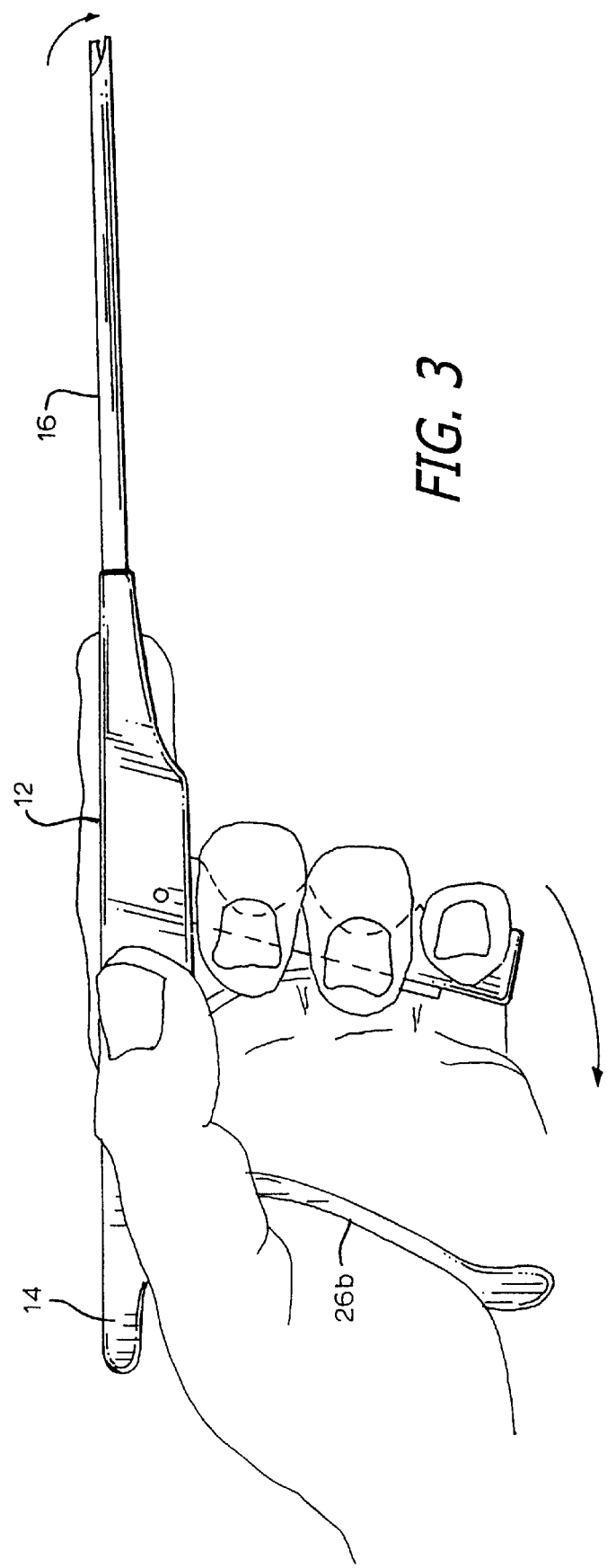
FIG. 3 is a side view of the surgical instrument of FIG. 1 as held in the hand of a surgeon in the retracted position.
Figure 5:
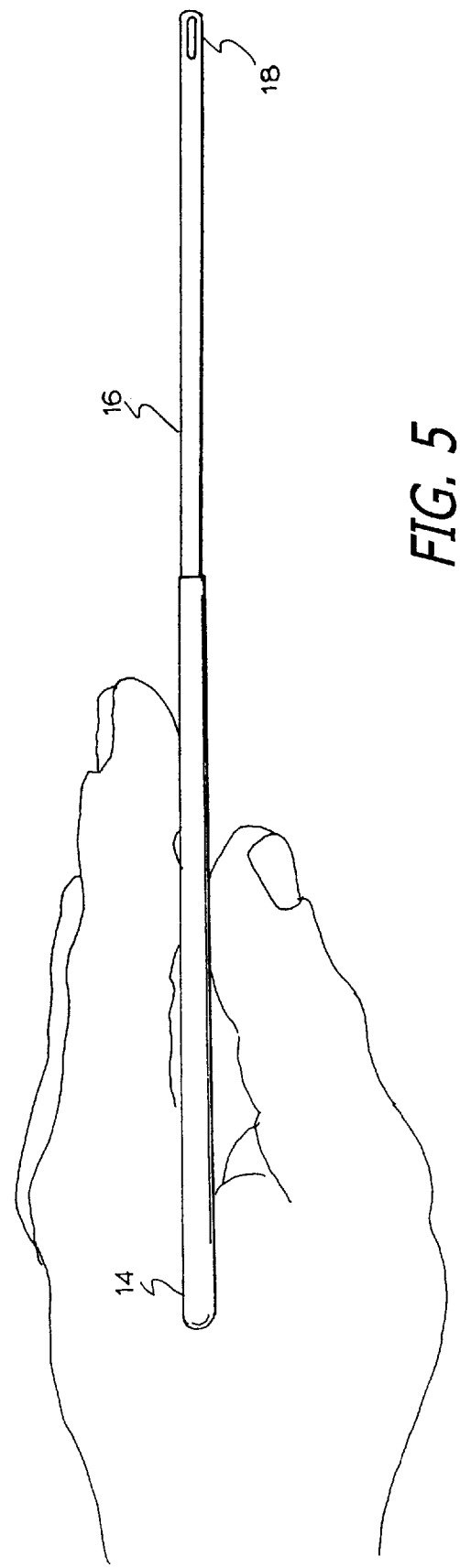
FIG. 5 is a top view of the instrument to the surgeon as viewed by him.

The front handle 22 is shaped for gripping by the remaining three fingers and for actuating the instrument. The front handle 22 is connected to the body portion 12 by pivot pin 24 or other means, at a position spaced forwardly from the rear handle 20 at a distance about equal to that distance between the joint of the thumb and the forefinger to the first finger joint of the middle finger. The portion of the body 12 where the thumb and index finger grasps the body portion is the pinch pad 17, as shown in FIG. 4. A portion 23 of the front handle further extends within the body portion 12 so that when the front handle 22 or trigger is pulled proximally about pivot pin 24, the jaws 18 of the biting instrument close. Though a push mechanism is described, pull and other mechanisms may be employed with the present invention as would be evident to those familiar with the art of fabricating surgical instruments.

The front handle 22 extends downwardly to accommodate the width of three fingers, so that as the instrument 10 is held, it is natural to extend the thumb and forefinger along the top of the body 12 directly in line with the working shaft 16 and to wrap the remaining fingers about the front handle. Indentations 28, 30 and 32 provide placement of these fingers.

A spring mechanism 34, or any other internal, external, or combination thereof, is utilized to urge the pivotable front handle 22 or trigger to its normal position.

The instrument is grasped quite differently from other surgical instruments, in that the index finger is separated from the remaining three fingers and is forced to extend along the main member of the body of the handle, while the three remaining fingers are wrapped around the shorter front handle, which serves in the embodiments shown, as the trigger.

Thus, the fingers of the hand do not engage the rear handle 20, contrary to the conventional instruments. Also, the index finger and the thumb of the surgeon do not engage the front handle, but come to rest on the pinch pad 17, a position which permits and promotes the advantages set forth above. Note that the portion of the hand, as shown in FIGS. 2–5, is below the plane of the top surface of the instrument and the handle.

While the present invention has been described in terms of the preferred embodiment in association for use with a rongeur, it may be used with other instruments, including, but not limited, scissors or the like, guns or staplers. Also, it is recognized that the size of the instrument can be varied, without departing from the present inventive concept.

Figure 6:
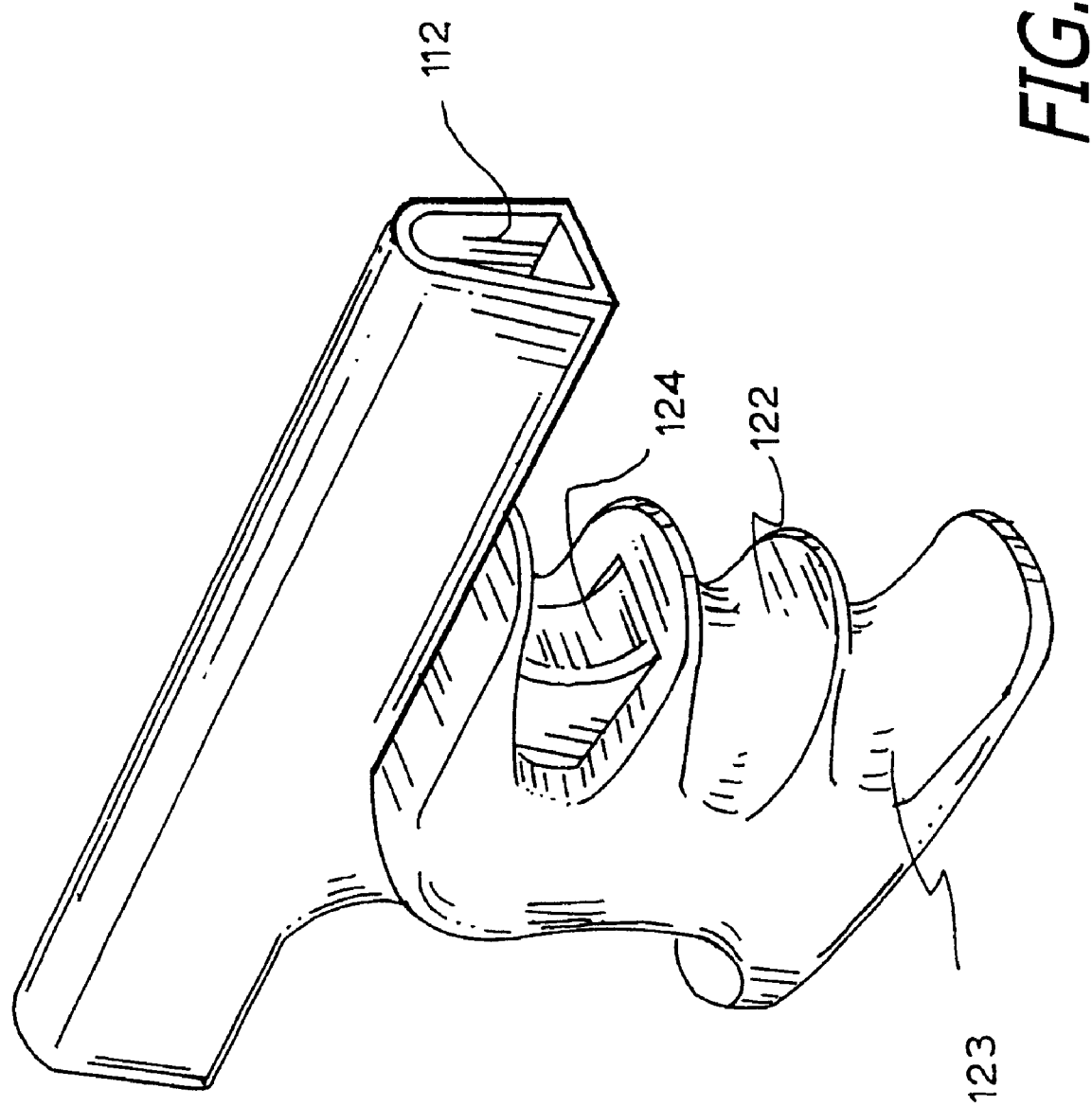

Referring to FIGS. 6–8 alternative embodiments of the present invention are shown, in which the handle is in the form of a gun butt, with a separate trigger mechanism.

In FIG. 6 the handle 110 has a replaceable instrument receiving housing 112 for permitting interchangable instrument tips to be used with the basic handle design. The front handle 122 receives the lower three fingers of the hand, and has a trigger 124 for activating the mechanism.

In FIG. 7, a handle 212 is shown for use with a gun. The gun has a body portion 12 with a barrel 226. The tip of the gun may have a front bead. Handle 212 has a rear 20 and a front 22 and depends from body portion 12. Body portion 12 has a proximal extension 14 at its rear end which joins rear 20 of handle 212 to form a rearwardly facing continuous curved portion 26. Proximal extension 14 extends for approximately one inch over the dorsum of the hand, specifically in the notch formed by the junction of the thumb and index finger.

Rear 20 of handle 212 extends substantially at right angles to body portion 12 and is in the shape of a rearwardly facing thenar fitting curve 26b formed to lie comfortably in the hand, cradled along the thenar-palm of the hand such that the palm closely fits up to the gun with the thumb and forefinger naturally extending on both sides of body portion 12, each projecting distally along a respective side at the top of body portion 12. Rear 20 of handle 212 anatomically conforms to the shape of the thenar eminence (the prominence of the muscles of the thumb) when the hand is in position with the index finger pointing and the thumb in an extended position. In fact, the hand, in grasping the gun, will, by means of the fixed rear handle contour, be coaxed into assuming the described position.

The portion of the rear handle 20 below of the thenar cradle portion, continues where it may form a reverse curvature to become convex or continue in line with the thenar portion such that the ulnar border of the hand is driven to a more proximal position beneath the thenar's and with a tenancy for the wrist to assume a more extended or cocked-up position.

Front 22 of handle 212 extends downwardly to accommodate the width of the bottom three fingers of the hand, so that as the gun is held, it is natural to extend the thumb and forefinger along the top of body 12 directly in line with barrel 226 and to wrap the remaining fingers about the front handle. Indentations 28, 30 and 32 provide placement of these fingers. Front 22 of handle 212 has a trigger 224 that is activated by the middle finger, with the thumb and fore finger pinching barrel 226 of the gun.

What is claimed is:

1. A gun comprising a body having therein a barrel with a longitudinal axis, said body having a rear and a front, a handle depending downwardly from said body, said handle having a thenar fitting concave curve adapted to conform to the natural curvature of the thenar eminence of the palm of a user's hand and facing said rear of said body, said rear of said body including a proximal extension extending rearwardly proximate a juncture of said body and said handle, said proximal extension adapted to extend over the dorsum of the user's hand and having a bottom surface adapted to contact the top of the dorsum, said body having sides at least in part parallel to the longitudinal axis of said barrel configured to be grasped by the thumb and the index finger of the user's hand, said sides being adapted to permit the placement of the thumb and the index finger of the user's hand generally parallel to and facing one another and generally in line with the longitudinal axis of said barrel, whereby when the user's hand is placed on said handle, the dorsum is in contact with said bottom surface of said proximal extension, the thenar eminence is in contact with said thenar fitting concave curve, and the index finger and the thumb of the user's hand are placed adjacent to said body and parallel to the longitudinal axis of said barrel, and a trigger, said handle having only two indentations below said trigger for placement of a user's finger.

2. The gun of claim 1, further comprising a front bead at a tip of said gun.

3. The gun of claim 1, further comprising a trigger.

4. The gun of claim 3, wherein said trigger is positioned on said handle and is configured for actuation by a user's middle finger.

5. A gun comprising a body having therein a barrel with a longitudinal axis, said body having a rear and a front, a handle depending downwardly from said body, said handle having a thenar fitting concave curve adapted to conform to the natural curvature of the thenar eminence of the palm of a user's hand and facing said rear of said body, said rear of said body including a proximal extension extending rearwardly proximate the juncture of said body and said handle, said proximal extension adapted to extend over the dorsum of the user's hand and having a bottom surface adapted to contact the top of the dorsum, said body having sides at least in part parallel to the longitudinal axis of said barrel configured to be grasped by the thumb and the index finger of the user's hand, said sides being adapted to permit the placement of the thumb and the index finger of the user's hand generally parallel to and facing one another and generally in line with the longitudinal axis of said barrel, whereby when the user's hand is placed on said handle, the dorsum is in contact with said bottom surface of said proximal extension, the thenar eminence is in contact with said thenar fitting concave curve, and the index finger and the thumb of the user's hand are placed adjacent to said body and parallel to the longitudinal axis of said barrel, said proximal extension being adapted to extend at least one inch over the dorsum of the user's hand.

6. A gun comprising:

a body having a proximal end and a distal end, said body having a barrel therein with a longitudinal axis, said body being generally aligned with the longitudinal axis of said barrel;

a handle depending downwardly from said body, said handle having a proximally facing thenar fitting concave curve with a concavity adapted to conform to the natural curvature of the thenar eminence of the palm of the user's hand;

a proximal extension in line with the longitudinal axis of said barrel and proximate a junction of said body and said handle, said proximal extension adapted to extend over the dorsum of the user's hand and having a bottom surface adapted to contact the top of the dorsum, whereby the dorsum is in contact with said bottom surface, the thenar eminence of the user's hand is in contact with said thenar fitting concave curve, and the index finger and thumb of the user's hand are placed adjacent to said body and generally parallel to the longitudinal axis of said barrel, said body having sides generally parallel to the longitudinal axis of said barrel configured to be grasped by the thumb and index finger of the hand, whereby the thumb and index finger when placed on said sides are parallel and face one another; and a trigger, said handle having only two indentations below said trigger for placement of a user's fingers.

7. The gun of claim 6, further comprising a front bead at a tip of said gun.

8. The gun of claim 6, wherein said handle includes a plurality of indentations adapted to accommodate fingers other than the thumb and the index finger when said gun is being grasped by the user's hand.

9. The gun of claim 8, wherein said handle includes three indentations adapted to separate three fingers from each other while said gun is being grasped by the user's hand.

10. The gun of claim 8, wherein said handle includes a trigger at least in part within one of the indentations.

11. The gun of claim 10, wherein the exposed surface of said trigger is within the confines of one of the indentations.

12. The gun of claim 6, wherein said handle is adapted to accommodate at least two fingers of a user and includes a trigger adapted to be actuated by a user's middle finger.

* * * * *

UNITED STATES PATENT AND TRADEMARK OFFICE
CERTIFICATE OF CORRECTION

PATENT NO. : 6,609,322 B1
DATED : August 26, 2003
INVENTOR(S) : Gary Karlin Michelson, M.D.

It is certified that error appears in the above-identified patent and that said Letters Patent is hereby corrected as shown below:

Column 7,
Line 22, change "finger" to -- fingers --;
Line 25, change "claim 1" to -- claim 5 --; and
Line 26, change "claim 3" to -- claim 1 --.

Column 8,
Lines 34-40, delete in their entirety.
Line 41, change "claim 8" to -- claim 6 --, and change "wherein said handle includes a" to -- further comprising a third indentation wherein said --;
Line 42, after "trigger" insert -- is --; and change "one of the indentations" to -- said third indentation --;
Line 43, change "the" (second occurrence) to -- said trigger has an --, and delete "of";
Line 44, delete "said trigger is", and change "one of the indentations" to -- said third indentation --; and
Lines 45-47, delete in their entirety.

Signed and Sealed this

Thirteenth Day of July, 2004

JON W. DUDAS
*Acting Director of the United States Patent and Trademark Office*